(12) United States Patent
Imam et al.

(10) Patent No.: US 7,279,292 B2
(45) Date of Patent: Oct. 9, 2007

(54) METHODS FOR DIAGNOSIS OF LOW GRADE ASTROCYTOMA

(75) Inventors: S. Ashraf Imam, North Hollywood, CA (US); Sudarshan Malhotra, Glendale, CA (US)

(73) Assignees: Governors of the University of Alberta, Alberta (CA); Huntington Medical Research Institutes, Pasadena, CA (US)

( * ) Notice: Subject to any disclaimer, the term of this patent is extended or adjusted under 35 U.S.C. 154(b) by 0 days.

(21) Appl. No.: 11/506,688

(22) Filed: Aug. 17, 2006

(65) Prior Publication Data

US 2006/0281138 A1    Dec. 14, 2006

Related U.S. Application Data

(63) Continuation-in-part of application No. 10/269,773, filed on Oct. 10, 2002, now abandoned.

(60) Provisional application No. 60/328,917, filed on Oct. 11, 2001.

(51) Int. Cl.
*G01N 33/53* (2006.01)
(52) U.S. Cl. ..................................... 435/7.1
(58) Field of Classification Search ...................... None
See application file for complete search history.

(56) References Cited

U.S. PATENT DOCUMENTS 5,807,692 A * 9/1998 Kinzler et al. ............. 435/7.21

OTHER PUBLICATIONS

Bhatnagar et al., Cytobios, 1995, 82(331): 239-49.*
Malhotra et al., "A Monoclonal Antibody for Cytoskeletal Antigenic Determinant(s) Distinguishable from Glial Fibrillary Acidic Protein in Astrocytes", Microbios Letters, 1984, vol. 26, pp. 151-157.
Malhotra et al., "Diversity Among Reactive Astrocytes: Proximal Reactive Astrocytes in Lacerated Spinal cord Preferentially React with Monoclonal Antibody J1-31", Brain Research Bulletin, 1993, vol. 30, pp. 395-404.
Malhotra et al., "Novel Astrocytic Protein in Multiple Sclerosis Plaques", Journal of Neuroscience Research, 1989, vol. 22, pp. 36-49.
Predy et al., "A New Protein (J1-31 Antigen, 30kD) is Expressed by Astrocytes, Müller Glia and Ependyma", Bioscience Reports, 1987, vol. 7, No. 6, pp. 491-502.
Predy et al., "Enhanced Expression of a Protein Antigen (J1-31 Antigen, 30 Kilodaltons) by Reactive Astrocytes in Lacerated Spinal Cord," Journal of Neuroscience Research, 1988, vol. 19, pp. 397-404.
Singh et al., "A New 'Marker' Protein for Astrocytes", Bioscience Reports, 1986, vol. 6, No. 1, pp. 73-80.
Singh et al., "J1-31 Antigen of Astrocytes: Cytoplasmic and Nuclear Localization", Dendron, 1992, vol. 1, pp. 91-108.
Singh et al., "Novel Rod-Shaped Structures Identified in Glioma Cell Nuclei by Immunolabelling and Confocal Laser Fluorescence Microscopy", Biomedical Letters, 1994, vol. 50, pp. 163-172.
Stratagene Catalog, 1998, cover pg., p. 39.

* cited by examiner

*Primary Examiner*—Christopher H. Yaen
*Assistant Examiner*—Hong Sang
(74) *Attorney, Agent, or Firm*—Christie, Parker & Hale, LLP

(57) ABSTRACT

A method for identifying low grade astrocytoma cells in a sample is provided, wherein the method distinguishes between low grade astrocytoma cells and normal astrocytes, thus permitting early diagnosis of astrocytoma. The method uses antibody directed against J1-31 to test astrocytes in the sample for the presence or absence of J1-31 polypeptide, the low grade astrocytoma cells being characterized by the absence of J1-31 while normal astrocytes are characterized by the presence of J1-31.

11 Claims, 1 Drawing Sheet

METHODS FOR DIAGNOSIS OF LOW GRADE ASTROCYTOMA

CROSS-REFERENCE TO RELATED APPLICATION(S)

This application is a divisional application of U.S. patent application Ser. No. 10/269,773 filed Oct. 10, 2002, now abandoned which claims the benefit of U.S. Provisional Application Ser. No. 60/328,917, filed Oct. 11, 2001, the content of which is hereby incorporated by reference in its entirety.

FIELD OF THE INVENTION

The subject of the present invention is a method for using an antibody to detect the presence of a disease, and more specifically to distinguish low grade astrocytomas from normal reactive astrocytes.

BACKGROUND OF THE INVENTION

Astrocytomas are members of the glioma family of tumors; that is, tumors arising from glial cells. In the case of astrocytomas, the tumors arise from a type of glial cell called astrocytes.

Astrocytes, named by Spanish neuroanatomist Santiago Ramon y Cajal in 1913 after he discovered the star-shaped cells, are the major cell types of the central nervous system that responds to various pathological conditions, including trauma, ischemia, demyelination, inflammation, etc. In response to such pathological conditions, the normally quiescent astrocyte becomes "reactive," and may proliferate and migrate, exhibiting hypertrophy with increased expression of Glial Fibrillary Acidic Protein (GFAP), expression of cell surface MHC class I and II molecules, and producing various cytokines and growth factors.

Neoplastic transformation of astrocytes give rise to a variety of astrocytomas. Astrocytomas are generally grouped into two categories: low-grade (grades 1 and 2) and high-grade (grades 3 and 4). High-grade tumors grow rapidly and can easily spread throughout the brain, while low-grade astrocytomas are usually much more localized and grow slowly over a longer period of time. The prognosis for patients with high-grade astrocytomas is poor, with an average survival of 18 months for patients with grade 3 astrocytoma (with radiation therapy and chemotherapy) and an average survival of from 17 weeks (no treatment) to 51 weeks (with surgery and radiation treatment) for grade 4 astrocytomas.

Morphologically, low-grade astrocytomas are usually normal in appearance, making it difficult to distinguish low-grade astrocytoma cells from normal quiescent or reactive cells. Some grade 2 low-grade astrocytomas may be slightly abnormal in appearance, but are not easily detected by routine microscopic evaluation of tissue biopsy samples. By contrast, the high-grade astrocytomas are abnormal in appearance and show evidence of mitosis, making the cells easily identifiable by microscopic evaluation.

Visualization of astrocytes during microscopic evaluation of tissue sections is typically facilitated by staining the biopsy tissue sample with antibody to GFAP, a cytoskeletal protein expressed both in quiescent and reactive astrocytes and in low grade and high grade astrocytomas. Both monoclonal mouse and polyclonal rabbit anti-human GFAP antibodies have been developed that are specific against GFAP, not recognizing other intermediate filament proteins. These antibodies typically react with both astrocytes and astrocytoma cells, and thus do not serve to differentiate between normal and transformed cells beyond facilitating morphological inspection.

Although the prognosis for patients with grade 1 astrocytoma is good, with some patients known to live 30 years or more following diagnosis, the prognosis for patients with grade 2 low-grade astrocytoma is much less optimistic. Recent studies have indicated that the 5-year survival rate in grade 2 astrocytomas is about 34%. With radiation therapy, the 5-year survival rate increased to about 70%. It is apparent that early diagnosis, and thus early treatment, is important in treating patients with low-grade astrocytoma.

What is needed, therefore, is a reliable and efficient diagnostic procedure for differentiating low grade astrocytoma cells from active and quiescent normal astrocytes in tissue biopsies.

SUMMARY OF THE INVENTION

One aspect of the present invention is a method for identifying low grade astrocytoma cells in a sample containing astrocytes, comprising testing the astrocytes in the sample for the presence or absence of J1-31 polypeptide, the low grade astrocytoma cells being characterized by the absence of J1-31.

Another aspect of the present invention is a method for distinguishing low grade astrocytoma cells from normal astrocytes, the method comprising the steps of:
  providing a tissue sample from a site of a suspected astrocytoma;
  contacting the sample with antibody molecules immunoreactive with J1-31 protein, under conditions wherein the antibody molecules can form an immune complex with any J1-31 antigen in the sample;
  detecting cells in the sample in which the immune complex is present, thereby identifying cells expressing the J1-31 antigen; and
  detecting astrocytes present in the sample in which the immune complex is absent, thereby identifying low-grade astrocytoma cells.

Another aspect of the present invention is a method for identifying low grade astrocytoma cells in a sample, comprising the steps of:
  contacting the biological sample with anti-J1-31 antibody under conditions in which the antibody binds to J1-31 antigen in the sample;
  contacting the biological sample with a secondary antibody selected so as to form an immune complex with the anti-J1-31 antibody bound to J1-31 antigen;
  detecting cells expressing the J1-31 antigen by detecting the immune complex; and
  detecting astrocytes in the sample in which the immune complex is not present, to thereby identify low-grade astrocytoma cells.

Another aspect of the present invention is a kit for in vitro diagnosis of low grade astrocytoma comprising anti-J1-31 antibody, a medium suitable for formation of an antigen-antibody complex, and reagents for detection of the antigen-antibody complex.

Another aspect of the present invention is a kit for in vitro diagnosis of low grade astrocytoma comprising anti-J1-31 antibody and instructions for using anti-J1-31 antibody to distinguish between low grade astrocytoma cells and other astrocytes.

BRIEF DESCRIPTION OF THE DRAWINGS

These and other features, aspects and advantages of the present invention will become better understood with reference to the following description, appended claims, and accompanying drawings wherein:

DETAILED DESCRIPTION OF THE INVENTION

Figure 1:
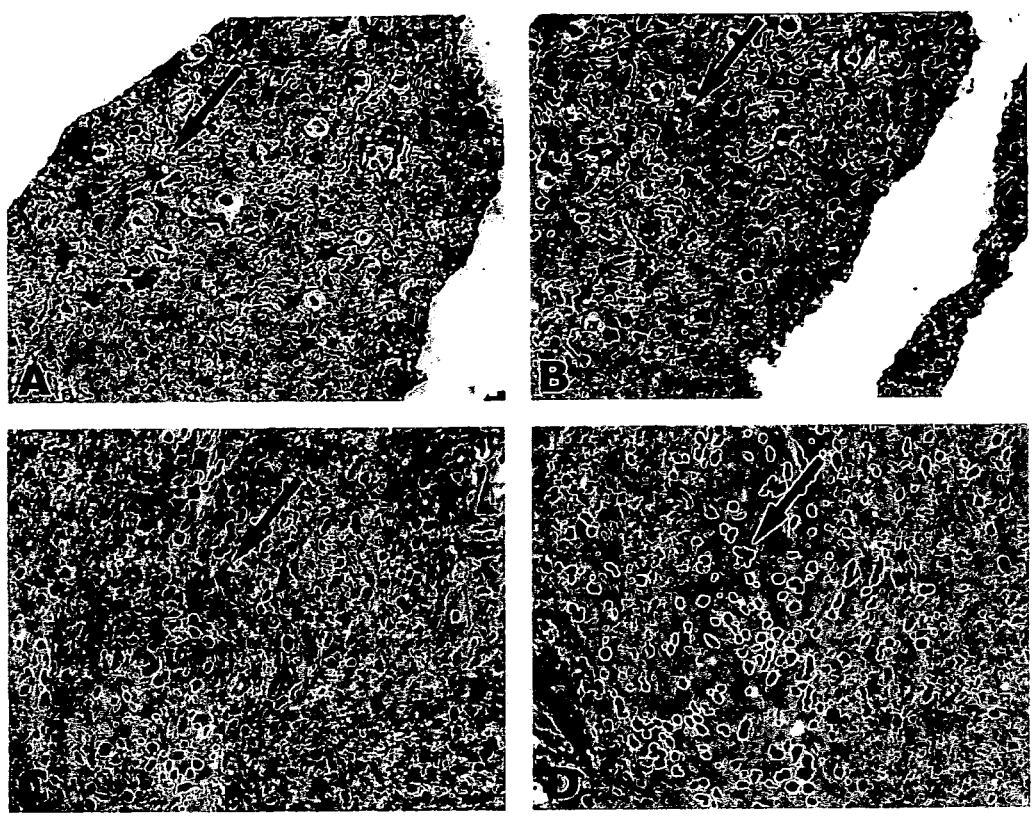
FIGS. 1A-1D show the immunohistochemical localization of J1-31 antigen and Glial Fibrillary Acidic Protein (GFAP) in formalin-fixed/paraffin-embedded tissue sections. Mouse monoclonal anti-J1-31 antibody or anti-Glial Fibrillary Acidic Protein (GFAP) antibody shows strong reactivity with normal astrocytes as shown by the arrow in FIGS. 1A (GFAP) and 1B (J1-31). The low grade (grade 2) astrocytoma cells showed no reactivity with anti-J1-31 antibody (arrow, FIG. 1D), whereas the surrounding normal astrocytes were positive (*, FIG. 1D). In contrast, anti-GFAP antibody reacted with both the normal astrocytes and the grade 2 astrocytoma cells (arrow, FIG. 1C). The tissue sections were counterstained with Harris hematoxylin (original magnification ×200).

The present invention relates to methods of identifying low grade astrocytoma cells and distinguishing such cells from normal, reactive astrocytes, using anti-J1-31 antibody.

One aspect of the method of the instant invention for identifying low grade astrocytomas comprises immunostaining tissue biopsy samples with anti-J1-31 antibody to differentiate between normal, reactive astrocytes and low grade astrocytoma cells.

Another aspect of the method of the instant invention for identifying low grade astrocytomas comprises immunolabeling tissue biopsy samples with anti-J1-31 antibody for fluorescence microcopy to differentiate between normal, reactive astrocytes and low grade astrocytoma cells.

Still another aspect of the method of the instant invention for identifying low grade astrocytomas comprises subjecting tissue biopsy samples to immunoelectron microscopy using anti-J1-31 antibody to differentiate between normal, reactive astrocytes and low grade astrocytoma cells.

Still another aspect of the method of the instant invention for identifying low grade astrocytoma cells comprises extracting proteins from tissue biopsy samples and immunoblotting with anti-J1-31 antibody to differentiate between normal, reactive astrocytes and low grade astrocytoma cells.

Still another aspect of the method of the instant invention comprises testing cultured cells for the presence of low grade astrocytoma cells using anti-J1-31 antibody.

Still another aspect of the present invention comprises kits useful for diagnosing low grade astrocytomas.

J1-31. J1-31 is a cytoskeleton-associated polypeptide, which has been shown to be a 30-kD protein, distinct from GFAP and vimentin proteins also found in glial cells. By contrast, GFAP is a major cytoskeleton protein.

The J1-31 polypeptide is expressed in both high grade astrocytoma cells and normal astrocytes, with enhanced expression demonstrated in reactive astrocytes following injury to the central nervous system (CNS). See, Singh, et al., (1986) *Bioscience Reports* 6: 73-80; Predy, et al., (1987) *Bioscience Reports* 7: 491-502; Predy, et al., (1988) *J. of Neuroscience Research* 19: 397-404; Malhotra, et al., (1989) *J. of Neuroscience Research* 22: 36-49; Singh, et al., (1992) *Dendron* 1: 91-108; Malhotra, et al., (1993) *Brain Research Bulletin* 30: 395-404; and Singh, et al., (1994) *Biomedical Letters* 50: 163-172, all hereby incorporated by reference in their entireties.

Surprisingly, however, the present invention demonstrates that J1-31 does not appear to be expressed in low grade astrocytoma cells. Thus, J1-31 is useful as a diagnostic tool for distinguishing low grade astrocytoma cells from quiescent and reactive astrocytes, as well as from high grade astrocytomas.

Antibodies. The present invention contemplates the use of polyclonal and monoclonal antibodies, including recombinant single-chain or other antibody derivatives or fragments, against J1-31 polypeptide and fragments thereof.

The present invention also contemplates the use of polyclonal and monoclonal antibodies against variants of J1-31 polypeptides, including naturally occurring allelic variants.

As used herein, unless specified to the contrary, "anti-J1-31 antibody" shall refer to a polyclonal or monoclonal antibody, including recombinant single-chain or other antibody derivatives or fragments, directed against J1-31 polypeptide(s) or fragments or variants thereof.

Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991) which is incorporated herein by reference, and Ausubel et al., (1994-1998, supra), in particular Section III of Chapter 11.

Alternatively, monoclonal antibodies may be produced using the standard method as, for example, described in an article by Kohler and Milstein (1975, Nature 256, 495-497) which is herein incorporated by reference.

Anti-J1-31 Monoclonal Antibody. One example of an anti-J1-31 monoclonal antibody was produced using tissue homogenate from the brain of a multiple sclerosis patient and hybridoma technology, as reported by S. K. Malhotra, et al., (1984) in *Microbios Letters* 26: 151-157, hereby incorporated by reference in its entirety. This anti-J1-31 monoclonal antibody is specific for astrocytes but recognizes different antigenic site(s) than does anti-GFAP antibody. Specifically, this anti-J1-31 monoclonal antibody reacts with the astrocytic cytoskeleton. The J1-31 hybridoma cell line has been deposited with the ATCC as CRL-2253.

Detection of Low Grade Astrocytoma Cells. As discussed above, it has been previously demonstrated that J1-31 polypeptide is expressed in normal astrocytes and in high grade astrocytomas, and may be detected in those cells using an anti-J1-31 monoclonal antibody. The present inventors have now found that J1-31 polypeptides are not detected in low grade astrocytomas, providing a new diagnostic method for identifying low grade astrocytoma cells, and thus facilitating earlier diagnosis and treatment of patients with low grade astrocytoma.

In the practice of this invention, astrocytes are tested using anti-J1-31 antibody, as described below. Optionally, the cells are also stained with a non-cell specific stain, as with Harris hematoxylin, for example, which stains cell nuclei a deep blue color, allowing all cells to be easily visualized. Optionally, cells may also be stained with anti-GFAP antibody, to facilitate characterization of the morphology of the astrocyte/astrocytoma.

Following testing with the anti-J1-31 antibody, the astrocytes are examined for the presence or absence of the J1-31 antigen and are identified, as summarized below in Table 1.

TABLE 1

| Cell Type | Morphologically Abnormal | Reacts with Anti-J1-31 Antibody |
| --- | --- | --- |
| Normal Astrocyte | No | Yes |
| Reactive Astrocyte | No | Yes |
| Low Grade Astrocytoma | No | No |
| High Grade Astrocytoma | Yes | Yes |

Thus, cells that appear as relatively morphologically normal astrocytes, but which do not contain J1-31 antigen, are identified as low grade astrocytoma cells.

Methods for Detecting J1-31 in Cells. As will be appreciated by the skilled practitioner, there are several ways known in the art for detecting the presence of a specific polypeptide in a cell. Some of these methods are discussed below. However, the present invention contemplates any technique whereby the presence or absence of J1-31 in a cell, either cultured or in a tissue sample, may be determined.

Immunohistochemical Staining of Tissue Sample

Screening techniques such as Magnetic Resonance Imaging (MRI) are used to identify potential brain tumor sites, and biopsy tissue, as from a needle biopsy, is extracted from patients for analysis.

Such clinically obtained tissue samples are generally formalin—fixed and paraffin—embedded, although tissue samples may also be fresh/frozen. Both are suitable for use in the present invention for immunohistochemical staining using an antibody directed to J1-31 protein. The tissue samples are then examined microscopically for the presence or absence of the J1-31 antigen in cells of interest. The procedure for preparing and staining these tissue samples is described below in detail.

Prior to immunohistochemical staining, slides containing the formalin-fixed/paraffin-embedded tissue biopsy samples are warmed overnight at 60° C. Slides containing fixed tissue are incubated twice for 5 minutes each in Histoclear, a clearing agent available from National Diagnostics, Atlanta, Ga., followed by two incubations of 3 minutes each in absolute ethanol and two incubations of 3 minutes each in 95% ethanol.

Slides containing formalin-fixed tissue samples that have been treated as described above with Histoclear and ethanol, are incubated for 20 minutes in a mixture of hydrogen peroxide and methanol. One suitable $H_2O_2$:methanol mixture is formed by adding 50 ml of 3% $H_2O_2$ to 200 ml methanol.

The slides are next washed for 5 minutes in Delbecco phosphate buffered saline (DPBS). A 10× stock of DPBS is made by combining 11.5 g dibasic sodium phosphate (molecular weight [m.w.] 142.0), 2.0 g monobasic potassium phosphate (m.w. 136.1), 2.0 g potassium chloride (m.w. 76.6) and 80.0 g sodium chloride (m.w. 58.5), and adding $dH_2O$ to a final volume of 1 liter. A 1× working stock of DPBS is prepared by mixing 100 ml 10×DPBS with 900 ml $dH_2O$.

Following the DPBS wash, slides are placed in an antigen unmasking solution (0.1 M sodium citrate, pH 6.0), placed in a pressure-cooker, and heated in a microwave oven at 600 W twice for 15 minutes each. The antigen unmasking solution is made by mixing 810 ml of 0.1 M sodium citrate·$2H_2O$ (m.w. 294.12; 29.4 g/1000 ml) with 190 ml of 0.1 M citric acid·$H_2O$ (m.w. 210.14; 5.252 g/250 ml), for a final volume of 1 liter. Following the microwave treatment, the slides are left in the antigen unmasking solution for an additional 20 minutes at ambient temperature.

Prior to immunohistochemical staining of freshly frozen tissue biopsy sections on glass slide, the fresh frozen biopsy sections are fixed in cold-acetone for 5 minutes, air-dried for 30 minutes and incubated twice in DPBS for 5 minutes each.

The slides containing formalin-fixed or acetone-fixed tissue sections are next incubated for 20 minutes in a 1:20 dilution of non-immune horse serum to prevent nonspecific binding, (Cat. No. S-2000), available from Vector Laboratories, Burlingame, Calif. This is followed by incubation in appropriate dilutions of the anti-J1-31 mouse monoclonal antibody from 60 minutes to overnight. The appropriate dilution of the antibody is dependent on a number of factors, including the concentration of the antibody being used, and may be determined empirically by techniques known to one skilled in the art.

Following incubation with the primary antibody, the slides are washed in DPBS four times, for two minutes each wash. The slides are then incubated in appropriate dilutions of biotinylated antibody for 30 minutes. One biotinylated antibody suitable for use with the anti-J1-31 mouse monoclonal antibody is a 1:200 dilution of biotinylated horse anti-mouse polyclonal antibodies (IgG, H+L), available from Vector Laboratories, Cat. No. BA-2000. This is followed by another series of four 2-minute washes in DPBS.

The slides are next incubated for 30 minutes in avidin-biotin-horseradish peroxidase complex (ABC), available in a kit from Vector Laboratories, Cat. No. PK-6100. In this procedure, a preformed Avidin (A):Biotinylated enzyme (B) complex is used with biotinylated antibodies. 25 µl each of the "A" and "B" reagents provided in the Vector kit are added to 2.45 ml DPBS for a final volume of 2.5 ml. Following incubation, the slides are washed 4 times for 2 minutes each in DPBS.

The final steps in the immunostaining procedure is to expose the slides with bound antibody-ABC to a chromogen substrate for the ABC enzyme. One chromogen suitable for use with horseradish peroxidase is diaminobenzidine (DAB).

Finally, the slides are incubated two-times in 95% ethanol for 3 minutes each incubation, followed by two 3-minute incubations in absolute alcohol, and ending with two 3-minute incubations in xylene. The slides are then provided with a coverslip in permount mounting medium.

Although one particular protocol has been described for use in immunohistochemical staining tissue samples with the anti-J1-31 mouse monoclonal antibody, other anti-J1-31 antibodies and immunostaining techniques may also be employed. For example, in addition to peroxidase conjugates, alkaline phosphatase conjugates may be used. Other suitable immunohistochemical procedures are apparent to the skilled practitioner.

Immunolabeling for Fluorescence Microcopy

Fluorescence microscopy may be used to detect J1-31 in astrocytes or high grade astrocytomas in cell culture or in tissue sections (Singh, supra, *Dendron* 1: 91-108).

Briefly, for cultured cells, coverslips bearing cells are fixed in either methanol (5 minutes at −20° C.) or 4% paraformaldehyde (30 minutes at room temperature). The coverslips are then washed in phosphate buffered saline (PBS), pH 7.4, containing 0.05% Tween-20 (PBS-T).

The coverslips with either an astrocytoma tissue section or cell line are incubated in 30% normal goat serum in PBS for 30 minutes to prevent non-specific binding. Anti-J1-31 antibody is added as the primary antibody and incubated overnight at 4° C. For example, antibody J1-31 ascites fluid may be applied at a 1:500 dilution in PBS; also, normal mouse serum (NMS; Sigma) may be applied to some coverslips as a control. Following a wash in PBS-T, an appropriate secondary antibody (for example, a 1:100 dilution in PBS of goat anti-mouse IgG conjugated to fluorescein isothiocyanate (FITC; Sigma)) is added and the coverslips incubated for one hour at room temperature in the dark.

Optionally, the cells are double-labeled by first washing the coverslips again in PBS-T, followed by the application of a second primary antibody and incubation overnight at 4° C. Suitable antibodies for double-labeling included rabbit anti-cow glial fibrillary acidic protein (GFAP; Dimension Laboratories; 1:500 dilution in PBS), and its control, normal rabbit serum (NRS; Sigma); alternatively, Mab Vim 13.2 (a monoclonal antibody to vimentin; Sigma) and its NMS control may be used, also at a 1:500 dilution. The coverslips are washed in PBS-T and goat anti-rabbit IgG-TRITC (Sigma) or goat anti-mouse IgM-TRITC (Sigma) is applied at a 1:100 dilution in PBS. The coverslips are then incubated in the dark for 1 hour at room temperature Following incubation, the coverslips are given a final wash in PBS-T, mounted in glycerol/□-phenylenediamine and viewed by fluorescence microscopy and laser scanning confocal microscopy. Those cells expressing J1-31 antigen, and thus incorporating anti-J1-31 antibody and FITC-labeled secondary antibody, will fluoresce at a particular wavelength when excited, while any low grade astrocytoma cells present in the sample will not fluoresce at that wavelength, as no anti-J1-31 antibody/FITC-labeled secondary antibody is incorporated, allowing the low grade astrocytoma cells to be distinguished from the J1-31 containing normal astrocytes and high grade astrocytomas. Where double labeling is used, the second fluorescent dye is selected so as to fluoresce at a different wavelength (or in response to a different excitation wavelength).

For immunofluorescence microscopy of tissue sections, the tissue sections are fixed in either 4% paraformaldehyde or methanol and sectioned using a cryostat or vibratome. Imprints on coverslips from fresh specimens may also be similarly fixed. Sections and imprints are immunostained as described above.

Other fluorescent dyes, known in the art, may also be used in the practice of the present invention.

Immunoelectron Microscopy

Immunoelectron microscopy can also be used to detect GFAP and J1-31 proteins at the ultrastructural level in biopsy samples (Singh, supra, *Dendron* 1: 91-108). Briefly, specimens are fixed in 1.25% glutaraldehyde and embedded in LR white resin by routine methods. Ultrathin sections are etched with sodium metaperiodate and double-immunolabeled with anti-J1-31 antibody (preferably, monoclonal anti-J1-31 antibody) and anti-GFAP antibody as primary antibodies. The presence of J1-31 and/or GFAP is detected by the presence of the primary antibodies, as determined using secondary antibodies labeled with gold particles of distinct size (for example, 5 nm for anti-J1-31 antibody and 10 nm for anti-GFAP antibody).

Thus, cells displaying both 5 nm and 10 nm particles (those expressing both J1-31 and GFAP; i.e., normal astrocytes and high grade astrocytomas) may be distinguished from astrocytes displaying only 10 nm particles (those expressing GFAP but not J1-31; i.e., low grade astrocytoma cells).

SDS-PAGE and Immunoblotting

The presence (or absence) of J1-31 in cells, both cultured and in tissue specimens, may be evaluated using standard sodium dodecyl sulfate polyacrylamide gel electrophoresis (SDS-PAGE) and western blot protocols, which also allow the determination of the molecular weight of J1-31 protein (Singh, supra, *Dendron* 1: 91-108).

Protein extracts from cultured cells (or tissue homogenates) are electrophoresed under reducing conditions in a discontinuous gel, then transferred to nitrocellulose or other suitable membrane by electrophoretic or other transfer. The membranes are then treated with anti-J1-31 primary antibodies and labeled secondary antibodies, using standard western blot procedures.

In one embodiment, suspected astrocytoma cells can be selectively dissected from tissue samples using, for example, the laser microdissection technique of PALM® (P.A.L.M. Microlaser Technologies AG, Germany). Protein extracted from these cells can then be subjected to SDS-PAGE/ western analysis to evaluate the presence or absence of J1-31.

Kits for the Detection of J1-31

For diagnosis of low grade astrocytomas, a kit for the detection of J1-31 in tissue specimens and/or cultured cells is used. The kit comprises anti-J1-31 antibody, optionally J1-31 antigen for use as a control, and a means for detecting the complexing of the antibody with J1-31 antigen in the cultured cells or tissue specimen.

The kit detects the J1-31 antigen, when present, with the anti-J1-31 antibody. The complexing immunoreaction is detected by staining, fluorescence, immunoprecipitation or by any other means used in the art and suitable for these purposes.

In addition to the above, the kits may also comprise control compounds, anti-antibodies, protein A/G, anti-GFAP antibodies and the like for use in double-labeling, etc., suitable for conducting the different assays referred to above.

Having generally described the invention, the same will be more readily understood through reference to the following example, which is provided by way of illustration, and is not intended to be limiting of the present invention.

EXAMPLE 1

Localization of J1-31 Antigen and Glial Fibrillary Acidic Protein (GFAP) in Formalin-Fixed/Paraffin-Embedded Tissue Sections Using Immunohistochemical Staining Formalin-fixed and paraffin-embedded tissue sections of a low grade astrocytoma were prepared and stained, as described above. Briefly, the tissue sections were treated as follows:

1. Slides of the tissue sections were warmed overnight at 60° C.
2. The slides were incubated in Histoclear for 5 minutes; repeated once.
3. The slides were incubated in absolute ethanol for 3 minutes; repeated once.
4. The slides were incubated in 95% ethanol for 3 minutes; repeated once.
5. The slides were incubated in $H_2O_2$:methanol for 20 minutes.
6. The slides were washed in DPBS for 5 minutes.

7. The slides were treated in antigen unmasking solution (0.1 M sodium citrate buffer, pH 6.0) in a pressure-cooker and heated in a microwave oven at 600 W twice for 15 minutes each.
8. The slides were left in the antigen unmasking solution for an additional 20 minutes at ambient temperature.
9. The slides were incubated in non-immune horse serum for 20 minutes.
10. The slides were incubated overnight in a humidified chamber in either a 1:1,000 dilution of anti-J1-31 monoclonal mouse antibody or a 1:50 dilution of 113 µg/ml monoclonal mouse anti-human GFAP antibody (Cat. No. M 0761, Dako Corporation, Carpenteria, Calif.).
11. The slides were washed in DPBS for 2 minutes; repeated three times.
12. The slides were incubated in a 1:200 dilution of biotinylated horse anti-mouse polyclonal antibodies for 30 minutes.
13. The slides were washed in DPBS for 2 minutes; repeated three times.
14. The slides were incubated in avidin-biotin-horseradish peroxidase complex (Vector Labs PK-6100 Elite) for 30 minutes.
15. The slides were washed in DPBS for 2 minutes; repeated three times.
16. The slides were incubated for 10 minutes in diaminobenzidine.
17. The slides were washed in water for two minutes; repeated four times.
18. The slides were incubated in Harris hematoxylin for 2 minutes.
19. The slides were washed in water for two minutes; repeated four times.
20. The slides were incubated in 95% alcohol for 3 minutes; repeat once.
21. The slides were incubated in absolute alcohol for 3 minutes; repeat once.
22. The slides were incubated in xylene for 3 minutes; repeat once.

The slides were then prepared in permount mounting medium and examined microscopically at 200× magnification. Photomicrographs of the stained cells are shown in FIGS. 1, A through D.

Cells stained with anti-J1-31 antibody are shown in FIGS. 1B and 1D, while cells stained with anti-GFAP antibody are shown in FIGS. 1A and 1C. As shown in FIGS. 1A and 1B, mouse monoclonal anti-GFAP antibody or anti-J1-31 antibody shows strong reactivity with normal astrocytes as shown by the astrocytes stained in brown (for example, by the arrow in FIGS. 1A (GFAP) and 1B (J1-31)).

The low grade (grade 2) astrocytoma cells, however, show no reactivity with anti-J1-31 antibody (note the absence of brown staining, for example, near the arrow, FIG. 1D), whereas the surrounding normal astrocytes were positive (note the presence of brown staining near the *, FIG. 1D). The blue-stained nuclei from the Harris hematoxylin counterstain indicate the presence of cells. In contrast, anti-GFAP antibody reacted with both the normal astrocytes and the grade 2 astrocytoma cells (see, for example, the brown-stained cells near the arrow, FIG. 1C).

Thus, as demonstrated above, anti-J1-31 antibody can be used to quickly and efficiently diagnose the presence of low grade astrocytoma cells in a patient, allowing for improved screening and treatment of patients experiencing neurological cancer.

All patents, patent applications, and other publications mentioned in this specification are incorporated herein in their entireties by reference.

While this invention has been described in detail with reference to a certain embodiments, it should be appreciated that the present invention is not limited to those precise embodiments.

Rather, in view of the present disclosure which describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

What is claimed is:

1. A method for identifying low grade astrocytoma cells in a biological sample, comprising the steps of:
    preparing slides from a biological sample;
    serially incubating said biological sample in at least ethanol and hydrogen peroxide;
    heating said slides in an unmasking solution including a mixture of at least sodium citrate and citric acid;
    incubating the biological sample with anti-J1-31 antibody under conditions in which the antibody binds to J1-31 antigen in the sample, said anti-J1-31 antibody being produced by the hybridoma cell line J1-31, ATCC designation number CRL-2253;
    contacting the biological sample with a secondary antibody selected so as to form an immune complex with the anti-J1-31 antibody bound to J1-31 antigen;
    detecting cells expressing the J1-31 antigen by detecting the immune complex; and detecting astrocytes in the sample in which the immune complex is not present, to thereby identify low-grade astrocytoma cells.

2. The method of claim 1, wherein the secondary antibody is biotinylated.

3. The method of claim 2, wherein the immune complex is detected by contacting the sample with an avidin-peroxidase conjugate, followed by a chromogen suitable for use as a peroxidase substrate.

4. The method of claim 1, wherein the secondary antibody is labeled with a fluorescent dye.

5. The method of claim 1, wherein the secondary antibody is labeled with a metal particle.

6. The method of claim 1, wherein after incubating the biological sample with anti-J1-31 antibody, the slides are washed at least four times with a wash solution, wherein the wash solution includes at least an 0.5% solution of Tween-20.

7. The method of claim 1, wherein the biological sample is fixed in one of either paraformaldehyde or methanol.

8. The method of claim 1, wherein the sample is further stained with a non-cell specific stain.

9. The method of claim 1, further comprising the step of contacting the sample with anti-GFAP antibody under conditions in which the anti-GFAP antibody binds to GFAP antigen in the sample.

10. The method of claim 9, wherein the anti-GFAP antibody is labeled with fluorescent dye selected to fluoresce at a distinct wavelength.

11. The method of claim 1 further comprising, before the step of detecting:
    incubating the immune complex with a conjugate; and
    exposing the conjugated immune complex with a chromogen.

* * * * *